United States Patent
Gregory et al.

(10) Patent No.: US 9,066,671 B2
(45) Date of Patent: Jun. 30, 2015

(54) SYSTEM AND METHOD FOR EARLY BREAST CANCER DETECTION USING ELECTRICAL PROPERTY ENHANCED TOMOGRAPHY

(75) Inventors: William D. Gregory, Shorewood, WI (US); Christopher Gregory, Shorewood, WI (US)

(73) Assignee: WISYS TECHNOLOGY FOUNDATION, Madison, WI (US)

( * ) Notice: Subject to any disclaimer, the term of this patent is extended or adjusted under 35 U.S.C. 154(b) by 437 days.

(21) Appl. No.: 12/425,567

(22) Filed: Apr. 17, 2009

(65) Prior Publication Data

US 2009/0264791 A1      Oct. 22, 2009

Related U.S. Application Data

(60) Provisional application No. 61/045,736, filed on Apr. 17, 2008.

(51) Int. Cl.
*A61B 5/05* (2006.01)
*A61B 5/053* (2006.01)
*A61B 5/00* (2006.01)
*A61B 6/00* (2006.01)

(52) U.S. Cl.
CPC .............. *A61B 5/0536* (2013.01); *A61B 5/4312* (2013.01); *A61B 5/053* (2013.01); *A61B 6/502* (2013.01); *A61B 2562/0209* (2013.01); *A61B 2562/046* (2013.01)

(58) Field of Classification Search
CPC .... A61B 5/053; A61B 5/0536; A61B 5/4312; A61B 6/502; A61B 2562/046; A61B 2562/0209

USPC .......................................................... 600/547
See application file for complete search history.

(56) References Cited

U.S. PATENT DOCUMENTS

| | | | | |
|---|---|---|---|---|
| 6,236,886 | B1 * | 5/2001 | Cherepenin et al. | 600/547 |
| 6,560,480 | B1 * | 5/2003 | Nachaliel et al. | 600/547 |
| 6,993,383 | B2 * | 1/2006 | Assenheimer | 600/547 |
| 2002/0138019 | A1 * | 9/2002 | Wexler et al. | 600/547 |
| 2002/0183645 | A1 * | 12/2002 | Nachaliel | 600/547 |
| 2003/0004432 | A1 * | 1/2003 | Assenheimer | 600/547 |
| 2003/0055358 | A1 * | 3/2003 | Ko et al. | 600/547 |

(Continued)

OTHER PUBLICATIONS

TJ Kao et al; Regional Admittivity Spectra With Tomosynthesis Images for Breast Cancer Detection—Conf Proc IEEE Eng Med Biol Soc, 2007—iris.lib.neu.edu; Sci. vol. 873:30-41; 1999 EIT and Tomogynthesis co-registered The ACT 4; Rensselaer.

(Continued)

*Primary Examiner* — Devin Henson
(74) *Attorney, Agent, or Firm* — Quarles & Brady, LLP

(57) ABSTRACT

A system and method for detecting cancerous tissue in a subject is provided. More specifically, the present invention provides a system and method for non-invasively identifying cancerous regions in breast tissue. The system includes a sensor system, a drive system, and a processor. The sensor system includes a sensor plate and, similarly, the drive system includes a drive plate. A time-varying voltage is applied to the drive plate and induced currents are subsequently measured by the sensor plate. Signals indicative of an induced current are then acquired and analyzed by the processor to determine the spatial location of anomalous regions. Subsequently, the anomalous regions are characterized as either cancerous or non-cancerous.

6 Claims, 12 Drawing Sheets

(56) References Cited

U.S. PATENT DOCUMENTS

| | | | |
|---|---|---|---|
| 2003/0135131 A1* | 7/2003 | Scholz | 600/547 |
| 2003/0216664 A1* | 11/2003 | Suarez | 600/547 |
| 2004/0167421 A1* | 8/2004 | Gregory et al. | 600/547 |
| 2005/0004490 A1* | 1/2005 | Organ et al. | 600/547 |

OTHER PUBLICATIONS

G Boverman et al; The Complete Electrode Model for Imaging and Electrode Contact; P Experiments—iris.lib.neu.edu; Sci. Technol., 13, 2002, EIT and Tomogynthesis co-registered The ACT 4; Rensselaer.

Tzu-Jen Kao et al; A Compensated Radiolucent Electrode Array for Combined EIT and Mammography, EB Evaporator—censsis.neu.edu, Biomedical Engineering e-mail; neweij@rpi.edu Rensselaer Polytechnic Institute Web Site: http://www.rpi.edu/~neweij . . . Electrode Array & Tomosynthesis Mammography.

JC Newell: Regional Admittivity Spectra With Mammograms in Breast Biopsy Patients; IFMBE Proceedings; vol. 14/JC 6; p. 3921; 2007; Springer Engineering Troy NY 12180 USA 3 $3nsselaer.

C Tamma: EIT Spectroscopy in the Mammography Geometry Using ACT 4-censsis.neu.edu.

H Xia: Reginal Admittivity Spectra with Mammograms in Breast Biopys Patients; censsis.neu.edu.

William D Gregory et al: Electrical Property Enhanced Tomography (EPET); Eng. In Med. and Bio. Soc., Proc. of the 22nd Int. Conf. of IEEE 4, 2632-2635; Jul. 23-28, 2000.

Brown, et al., Tetrapolar Measurement of Cervical Tissue Structure Using Impedance Spectroscopy, Proceedings of the 20th Annual International Conference of the IEEE Engineering in Medicine and Biology Society, 1998, 20 (6):2886-2889.

\* cited by examiner

SYSTEM AND METHOD FOR EARLY BREAST CANCER DETECTION USING ELECTRICAL PROPERTY ENHANCED TOMOGRAPHY

CROSS-REFERENCE TO RELATED APPLICATIONS

This application is based on, fully incorporates herein by reference, and claims the benefit of U.S. Provisional Patent Application Ser. No. 61/045,736, filed on Apr. 17, 2008, and entitled "System and Method For Early Breast Cancer Detection Using Electrical Property Enhanced Tomography".

BACKGROUND OF THE INVENTION

The field of the invention is electrical property imaging systems and methods. More particularly, the invention relates to characterizing an anomaly in a tissue as pre-cancerous, cancerous, or non-cancerous.

Screening mammography has been the gold standard for breast cancer detection for over 30 years, and is the only available screening method proven to reduce breast cancer mortality. As a result, breast cancer mortality has decreased 25% since 1990. However, the sensitivity of screening mammography varies considerably. For example, the false-negative rate for mammography is around 20% and the false-positive rate around 12%. Moreover, radiologists cannot distinguish malignant and benign breast tissue by viewing a mammogram.

The most important factor in the failure of mammography to detect breast cancer is radiographic breast density. In studies examining the sensitivity of mammography as a function of breast density, the sensitivity of mammography falls from around 85% in women with fatty breasts to 48-63% in women with extremely dense breasts. Additional drawbacks of conventional mammographic screening include patient discomfort associated with the compression of the breast (mammography requires 45 pounds of pressure).

Screening alternatives to mammography include ultrasound and MRI. The effectiveness of whole-breast ultrasound as a screening technique, however, does not appear to be significantly different from mammography. Furthermore, while MRI has appreciable sensitivity for the detection for breast cancer and is not affected by breast density, the high cost of bilateral breast MRI (approximately 10 times more expensive than mammography) has precluded its widespread use as a screening technique. Other issues limiting the widespread use of MRI as a screening tool for breast cancer include the variability of the equipment involved, the long scan times often required for imaging session, the lack of clarity regarding the preferred imaging technique and result interpretation criteria, and its relative inability to reliably detect microcalcifications and DCIS. Furthermore, MRI has a higher false-positive rate compared to conventional mammography and performs poorly for detecting invasive lobular cancers.

A high percentage of breast cancers are not detected at the screening stage as standard mammographic images are one of the most difficult radiographic exams to interpret. Studies show that 20% to 50% of breast cancers go undetected at the screening stage. The motivation for early detection is great. For example, breast cancer detected in the early stage has an average cost of treatment of $11,000 and a 5 year survival rate of approximately 96%, while late stage breast cancer costs $140,000 on average to treat and the 5 year survival falls to 20%. Moreover, 5% of breast cancer tumors appear to double in size in just over a month.

After a suspicious lesion is found, medical professionals often rely on expensive biopsies to diagnose cancerous tissues. These procedures are neither fast nor patient-friendly. Surgical biopsy is recommended for suspicious lesions with a high chance of malignancy but fine-needle aspiration cytology (FNAC) and core biopsy can be inexpensive and effective alternatives. Both FNAC and core biopsy have helped to reduce the number of surgical biopsies, sparing patients anxiety and reducing the cost of the procedure. However, core biopsies have often failed to show invasive carcinoma and both FNAC and core biopsies can result in the displacement of malignant cells away from the target, resulting in misdiagnosis. Additionally, core biopsies have a limited sampling accuracy because only a few small pieces of tissue are extracted from random locations in the suspicious mass. In some cases, sampling of the suspicious mass maybe missed altogether. Consequences include a false-negative rate of 1-7% (when verified with follow up mammography) and repeat biopsies (percutaneous or surgical) in 9-18% of patients due to discordance between histological findings and mammography. The sampling accuracy of core needle biopsy is, furthermore, highly dependent on operator skills and on the equipment used.

Less invasive methods of diagnosing breast cancer, such as needle biopsy and sentinel node biopsy, can largely replace traditional open procedures, which still account for about one-third of the 1.7 million breast biopsies performed each year in the U.S. In a review of cytologic-histologic specimen pairs, errors in cancer diagnosis were seen in up to 11.8% of cases. In a substantial proportion of cases, the error caused some degree of harm for the patient. More specifically, up to 45% of errors resulted in harm to the patient, ranging from further unnecessary noninvasive diagnostic tests to loss of life or limb while up to 50% were due to pathologic misinterpretation. In the remainder of the cases, the errors were due to poor tissue sampling.

The biochemical properties of cancerous cells versus normal cells are characterized by three factors: increased intracellular content of sodium, potassium, and other ions; increased intracellular content of water; and a marked difference in the electrochemical properties of the cell membranes. The increased intracellular concentrations of sodium, potassium, and other ions result in higher intracellular electrical conductivity. Likewise, the increased water content results in higher conductivity when fatty cells surround the cancerous cells, since water is a better conductor than fat. In addition, the biochemical differences in the cell membranes of cancerous cells result in greater electrical permittivity.

A study of breast carcinoma described three separate classifications of tissue: tumor bulk, infiltrating margins, and distant (normal) tissue. The center of the lesion is called the tumor bulk and it is characterized by a high percentage of collagen, elastic fibers, and many tumor cells. Few tumor cells and a large proportion of normally distributed collagen and fat in unaffected breast tissue characterize the infiltrating margins. Finally, the distant tissues (2 cm or more from the lesion) are characterized as normal tissue.

The characterization of cancerous tissue is divided into two groups: in situ and infiltrating lesions. In situ lesions are tumors that remain confined in epithelial tissue from which they originated. The tumor does not cross the basal membrane, thus the tumor and the healthy tissue are of the same nature (epithelial). The electrical impedance of an in situ lesion is thus dependent on the abundance of the malignant cells that will impact the macroscopic conductivity (which is influenced by the increase in sodium and water) and permittivity (which is influenced by the difference in cell membrane electrochemistry).

By contrast, infiltrating lesions are tumors that pass through the basal membrane. The malignant tissue has a different nature than normal tissue (epithelial vs. adipose). Epithelial tissue is compact and dense. Adipose tissue is composed of large cells that are mostly triglycerides. These structural differences have the following impact. First, the normal tissue has a lower cellular density. Second, cell liquid of normal tissue is not as abundant as epithelial cells. Generally the radiuses of epithelial cells are less than adipose cells, from which flows the fact that the radius of cancerous cells is generally less than for normal cells. The impact on the fractional volume of cancerous cells versus normal cells is that the fractional volume of cancerous cells is greater than for normal cells. The reason for this is that the epithelial population is higher than for normal, adipose cells. Finally, the intracellular conductivity of cancerous cells is greater than for intracellular conductivity of normal cells. Moreover, the extracellular conductivity is higher because of the abundance of extracellular fluid resulting from larger gaps between normal and cancerous cells. Thus, the conductivity of the infiltrated tissue will be greater than for normal tissue.

Various studies show that the values of biological tissues resistivities vary for a host of reasons. Cancerous tumors, for instance, possess two orders of magnitude (factor of 100) higher conductivity and permittivity values than surrounding healthy tissue. The application of medical treatments also produces a change in the electrical properties of tissue. For muscle tissue treated with radiation, measurable changes to tissue impedance are reported. Significant changes occur in electrical impedance of skeletal muscle at low frequencies during hyperthermia treatment, and this change of electrical properties foreshadows the onset of cell necrosis.

Electrical impedance tomography (EIT) is a process that maps the impedance distribution within an object. This map is typically created from the application of current and the measurement of potential differences along the boundary of that object. There are three categories of EIT systems: current injection devices, applied potential devices, and induction devices. Henderson and Webster first introduced a device known as the impedance camera that produced a general map of impedance distribution. The Sheffield System and its incarnations were the first generation EIT system. In the late 1980's, Li and Kruger report on an induced current device. In such a system, a combination of coils is placed around the object under test. A changing current in the coils produces a varying magnetic field that in turn induces a current in the object under test. As with the other drive method, electrodes are placed on the boundary of the object to measure the potential drops along the boundary.

Such electrical property imaging techniques are often referred to as "impedance tomography." Most conventional electrical property imaging techniques are based on the premises that: 1) electrodes, or sensors, should be attached directly to the sample to be measured (for medical applications, the sample is a human body), and 2) current is injected sequentially through each electrode into the sample and the subsequent voltages measured. Therefore, these conventional EIT imaging techniques implement a "constant current/measured voltage" scheme.

In a departure from such conventional electrical property imaging techniques, U.S. Pat. No. 4,493,039 disclosed a method in which sensors are arranged in an array outside the object to be measured and during imaging of a sample, AC voltages are applied at a fixed amplitude while the current is measured. This approach, which is sometimes referred to as electrical property enhanced tomography (EPET), was further improved upon as described in U.S. Pat. No. 6,522,910 by filling the space between the object and the sensor array with an impedance matching medium.

SUMMARY OF THE INVENTION

The present invention provides a method for locating and characterizing anomalies in a tissue. More specifically, the present invention provides a system and method for non-invasively identifying anomalous regions within a portion of a subject by applying an electrical power to a portion of a subject and measuring a resulting electrical characteristic induced in the portion of the subject. This is a departure from previous methods that require the calculation of electrical properties of the tissues, such as impedance and dielectric constant, within the portion of the subject.

It is one aspect of the invention to provide a system for analyzing a portion of a subject so that a disease state of a region within the portion can be identified. The system includes a sensor system and a drive system, which are arranged parallel to each other such that a region is defined between them in which the portion of the subject is received during an examination. In one configuration, the sensor system includes a sensor plate that includes a guard plate and a segmented sensor array. Similarly, in one configuration the drive system includes a drive plate that is a continuous piece of stainless steel. However, in the alternative, the drive plate can include a guard plate and a segmented drive electrode array.

The system of the present invention further includes a processor for receiving electrical characteristics measured by the sensor system. In one configuration, the processor identifies anomalous regions within the portion of the subject that is being examined from these measured electrical characteristics. Changes in the measured electrical characteristics are then calculated and analyzed to determine the spatial location, both in a plane transverse to the sensor system and along an axis perpendicular to the sensor system, of anomalous regions in the portion of the subject. Further, in one configuration, after identifying and determining the spatial location of anomalous regions, the processor determines the disease state of the anomalous regions by correlating signal information corresponding to the anomalous regions to reference signal information.

It is another aspect of the invention to provide a method for identifying an anomalous region in a portion of a subject and determining a disease state of said anomalous region. A power is first applied to the subject and an electrical characteristic of the power is varied at a selected frequency. In one configuration the electrical characteristic is a voltage, and in another configuration the electrical characteristic is a current. A signal indicative of a second electrical characteristic, which is generated as a result of the applied power, is acquired. In one configuration, the second electrical characteristic is a current, and in another configuration the second electrical characteristic is a voltage. The spatial location of at least one anomalous region within the subject is then determined from the measured signal that is indicative of the second electrical characteristic. In one configuration, the spatial location includes both a location in a transverse plane and along an axis perpendicular to the plane. An anomalous region is then characterized as a particular disease state. In one configuration, the disease state includes cancerous and non-cancerous tissue.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE PREFERRED EMBODIMENT

Figure 1:
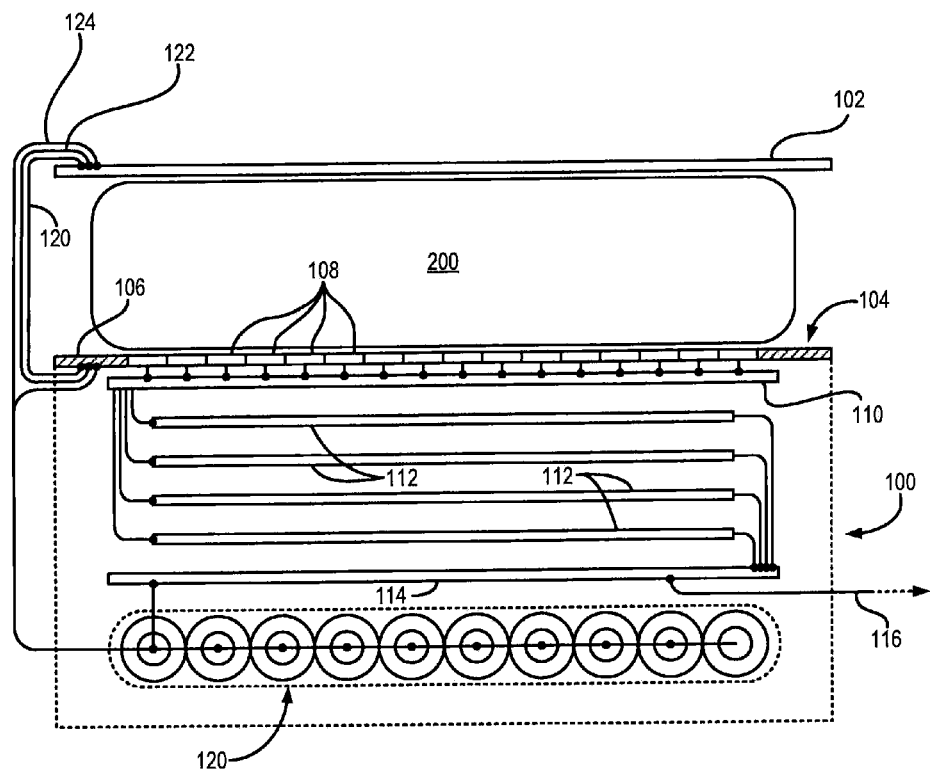
FIG. 1 is graphic representation of a cross-section of one embodiment of the system of the present invention.
Figure 2:
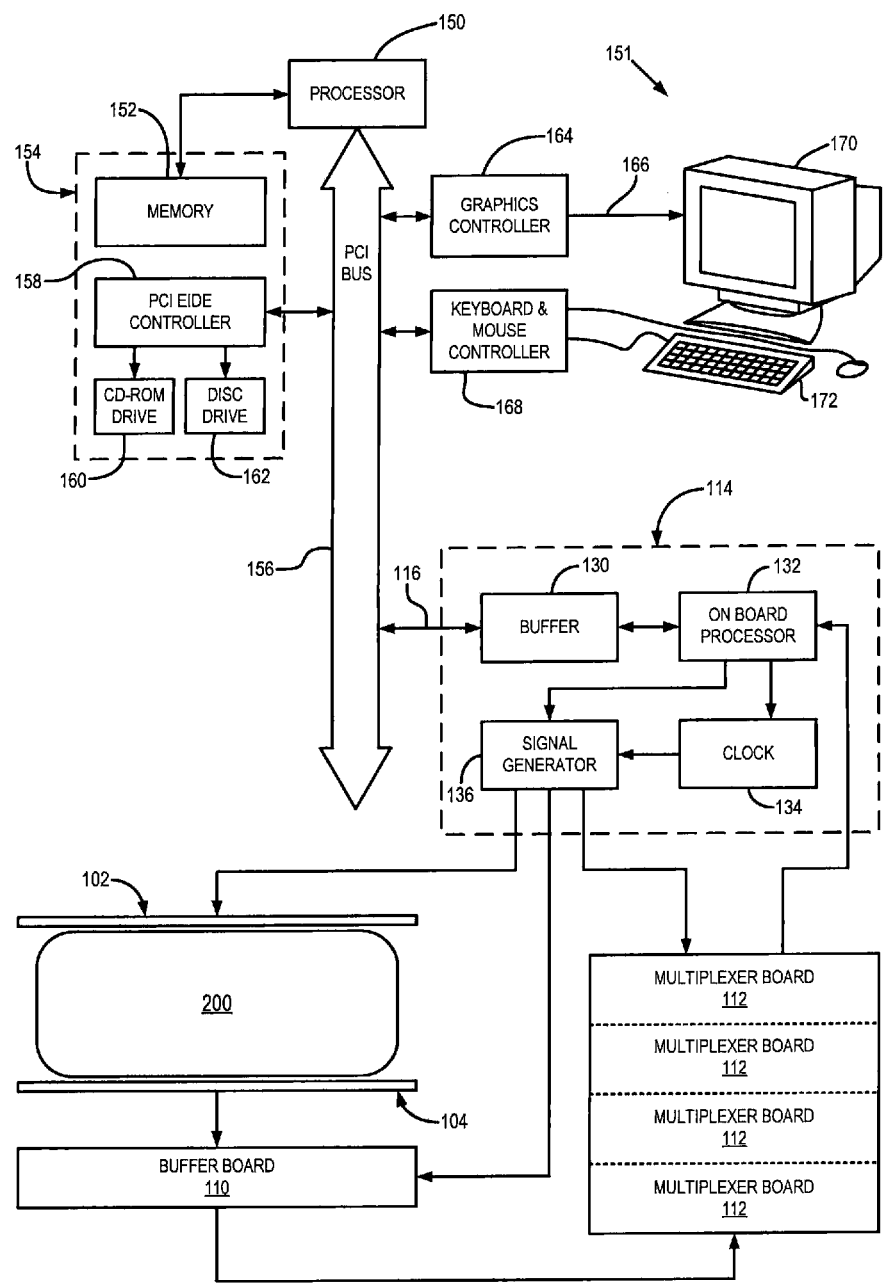
FIG. 2 is a block diagram showing an exemplary computer system useful for implementing the present invention.
Figure 3:
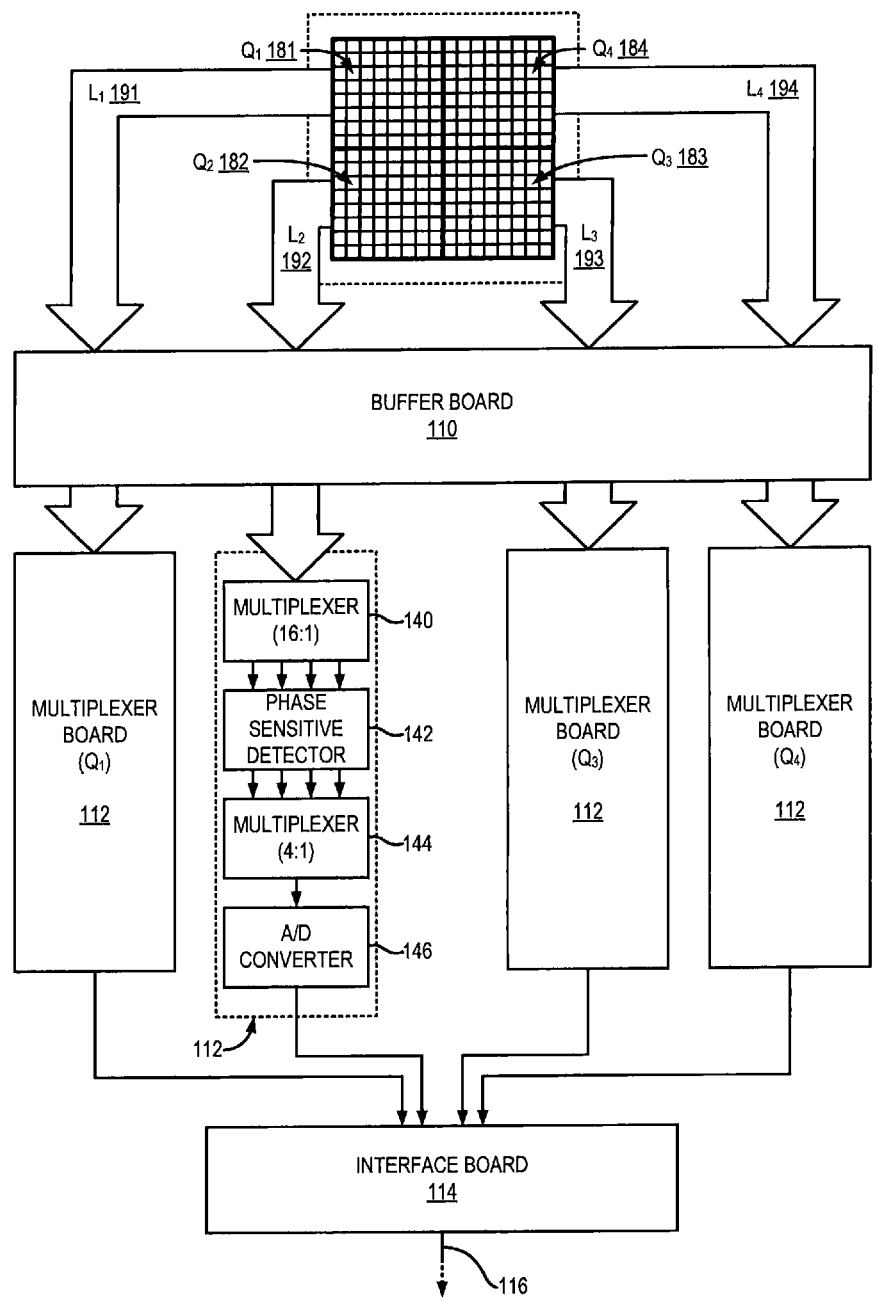
FIG. 3 is a block diagram of the sensor system which forms a part of the system of FIG. 1.

Referring particularly to FIGS. 1-3, a cross-sectional view of a device for acquiring information indicative of the electrical properties of an object is shown. The device includes a sensor system 100 and a drive plate 102 that are arranged to be parallel and spaced apart by a distance that allows for the reception of an object 200 for examination. The drive plate 102 is composed of titanium; however, it will be appreciated by those skilled in the art that other conductive metals can be employed in its construction. Preferably, the distance between the sensor system 100 and drive plate 102 is variable. The sensor system 100 includes a sensor plate 104, which further includes a guard ring 106 and an array of sensor elements 108. The sensor plate 104 may be composed of copper with a blackened platinum coating that is employed to reduce polarization charge effects. In the one configuration, the array of sensor elements 108 contains 256 isolated sensor elements 108 arranged in a 16×16 grid. The sensor plate 104 may be constructed using conventional lithography methods with copper. However, copper will not adhere to platinum without reacting, so the copper is first coated. This is accomplished using a sandwich of copper-nickel-gold, which is subsequently coated by platinum.

Each sensor element 108 is electrically connected to a buffer board 110. The buffer board 110 has formed thereon, current-to-voltage converters and low gain voltage follower buffers. As will be described in further detail below, the buffer board 110 is connected to a plurality of multiplexer boards 112 that perform phase sensitive detection on the measured signals, as well as analog-to-digital conversion and multiplexion. In one configuration, four multiplexer boards 112 are employed and the array of sensor elements 108 is divided into four quadrants containing sixty-four sensor elements 108 arranged in an 8×8 grid. In such an arrangement, a first 8×8 quadrant $Q_1$ 181 of sensor elements 108 is connected to a first multiplexer board 112, a second quadrant $Q_2$ 182 of sensor elements 108 is connected to a second multiplexer board 112, a third quadrant $Q_3$ 183 of sensor elements 108 is connected to a third multiplexer board 112, and a fourth quadrant $Q_4$ 184 of sensor elements 108 is connected to a fourth multiplexer board 112. The multiplexer boards are then connected to an interface board 114. As will be shown in more detail below, the interface board is connected to a processor 150 via a fiber optic cable 116 and a PCI bus 156. The sensor system also includes a power source 120. In one configuration, the power source includes a plurality of rechargeable batteries.

The drive plate 102 may be composed of titanium; however, it will be appreciated by those skilled in the art that other metals can be used in its construction. For example, stainless steel coated in blackened platinum can alternatively be used to form the drive plate 102. The drive plate may be a continuous, non-segmented plate or, in the alternative, it may be segmented into a guard ring and array of drive elements that mirrors the sensor plate 104. The drive plate 102 and sensor system 100 are connected via three cables: a ground cable 120, a signal cable 122, and a power cable 124.

Referring particularly to FIG. 2, a computer controller system 151 includes a processor 150 which executes program instructions stored in a memory 152 that forms part of a storage system 154. The processor 150 is a commercially available device designed to operate with, for example, a commercial operating system, such as those available from Microsoft Corporation. The computer controller system includes internal memory 152 and I/O controllers 158, 168. The computer controller system also includes a PCI bus drive, such as a 32-bit PCI bus.

The PCI bus 156 is an industry standard bus that transfers 32-bits of data between the processor 150 and a number of peripheral controller cards. These include a PCI EIDE controller 158 that provides a high-speed transfer of data to and from a CD ROM drive 160 and a disc drive 162. A graphics controller 164 couples the PCI bus 156 to a monitor 170 through a standard video connection 166, and a keyboard and mouse controller 168 receives data that is manually input through a keyboard and mouse 172. The PCI bus 156 also connects to the interface board 114 via a fiber optic link 116. The interface board 114 couples data to and from the sensor system 100 during the data acquisition phase of the procedure.

The interface board 114 includes a memory buffer 130, an onboard processor 132, a clock 134, and a signal generator 136. The digital signal outputted by the multiplexer boards 112 are received by the onboard processor 132 and sent to the buffer 130 for temporary storage. When the entire data acquisition process is completed, the onboard processor 132 initiates a transfer of the measured signals from the buffer 130 to the storage system 154 via the fiber optic link 116. The onboard processor 132 controls the clock 134 and signal generator 136 to apply a time-varying sinusoidal voltage having a selected frequency to the drive plate 102. The signal generator 136 and clock 134 can also be directed by the onboard processor 132 to provide reference signals for the phase sensitive detection process and a current bucking mode of operation, each of which will be described in more detail below.

Referring now to FIG. 3, a block diagram of the sensor system is shown. The array of sensor elements 108 is preferably divided into four quadrants: $Q_1$ 181, $Q_2$ 182, $Q_3$ 182, and $Q_4$ 184. In this manner, each quadrant comprises 64 sensor elements 108 arranged in an 8×8 array. An electrical connection is established between each individual sensor element 108 and the buffer board 110. Collectively, the electrical connection from the sensor elements 108 in quadrant $Q_1$ 181 follow path $L_1$ 191, the sensor elements 108 in quadrant $Q_2$ 182 follow path $L_2$ 192, the sensor elements 108 in quadrant $Q_3$ 183 follow path $L_3$ 193, and the sensor elements 108 in quadrant $Q_4$ 184 follow path $L_4$ 194. The current measured at each sensor element 108 is converted to a voltage using a standard current-to-voltage converter, after which the voltage signals pass through a low gain voltage buffer.

From the buffer board 110, an electrical connection is made to each of four multiplexer boards 112, where one board is supplied for each quadrant of the array of sensor elements 108. Therefore, in one configuration 64 voltage signals are passed to each multiplexer board 112. First, the 64 voltage signals are split into four different 16-to-1 multiplexers 140 that each multiplex 16 of the 64 voltage signals into one signal, resulting in four separate multiplexed signals. Following this process, the multiplexed signals are each passed through a phase sensitive detector 142, which acts to remove noise from the signals. The multiplexed signals are then further multiplexed in a 4-to-1 multiplexer 144. The resultant signal is converted from analog to digital through a 24-bit analog-to-digital converter 146. As a result, one digital signal is produced from each of the four quadrants: $Q_1$ 181, $Q_2$ 182, $Q_3$ 182, and $Q_4$ 184. These digital signals are stored in the memory buffer 130 on the interface board 114, as described above.

Figure 4A:
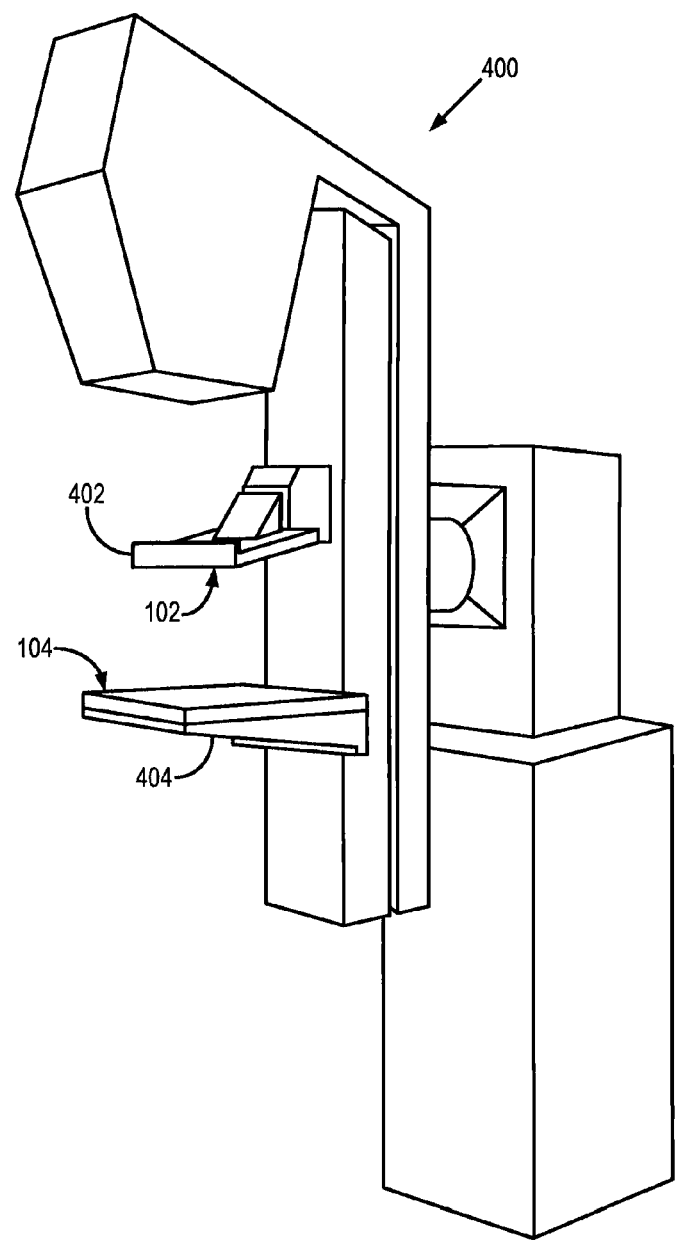
FIG. 4A is an x-ray mammography system, with which a configuration of the system of the present invention is integrated.
Figure 4B:
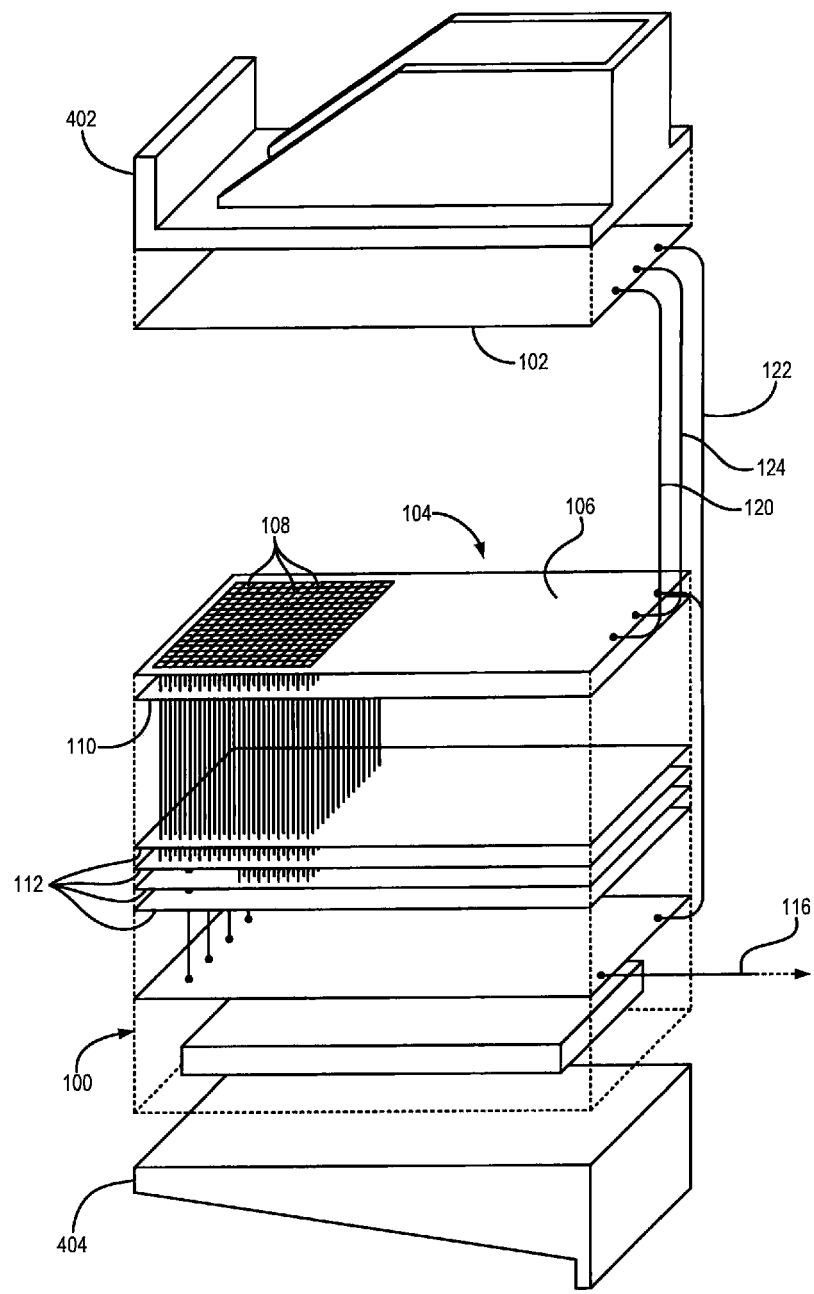
FIG. 4B is a graphic representation of the configuration of the system of the present invention, as integrated with the x-ray mammography system in FIG. 4A.

In one configuration of the present invention, the system of the present invention is integrated with an x-ray mammography system 400, as shown in FIGS. 4A and 4B. In this configuration, the drive plate 102 is attached to a compression paddle 402 and the sensor system 100 is attached to a film table 404 of the mammography system 400. The integration with a mammography system 400 allows for the augmentation of conventional breast cancer screening. Traditional mammography images can be acquired with the mammography system 400 and automatically co-registered with the data acquired by the imaging system of the present invention. Furthermore, by coupling the system of the present invention to a mammography system 400, the present invention can share the same viewpoint advantages as the mammography system 400. For example, should a more appreciable view angle of the subject's breast be required, the mammography system 400 can rotate the compression paddle 402 and film table 404 to accommodate the more desirable view angle. Since the system of the present invention is coupled to the mammography system 400, it will share the same desirable view angle. This allows more freedom when undergoing subject examination.

Figure 5A:
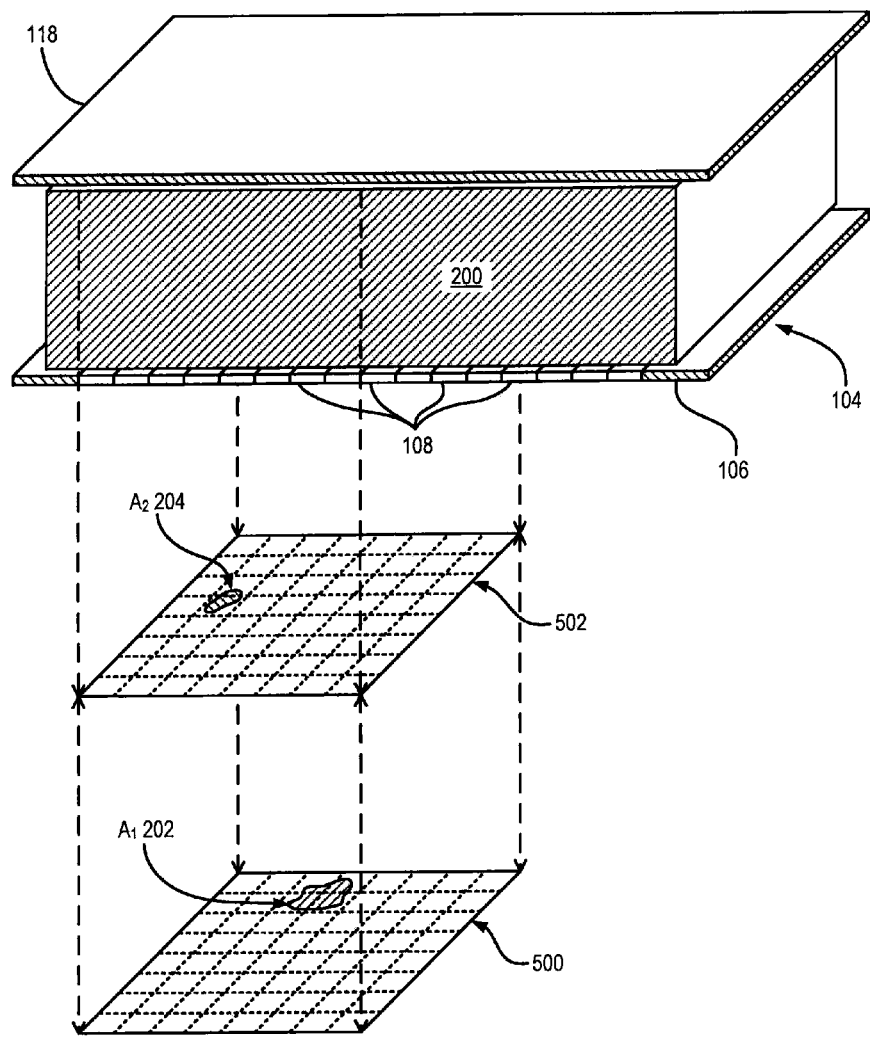
FIG. 5A is a graphic representation of a cross-section of the system of FIG. 1 and an example object under examination.

An exemplary analytical process will be described with respect to FIG. 5. In this example, an object 200 is placed between the sensor plate 104 and drive plate 102. Furthermore, the object 200 is positioned to lie substantially within a subset of the array of sensor elements 108, such as, for example, the 8×8 array of said sensor elements 108 shown in FIG. 3 as $Q_1$ 181. In this example, the object 200 includes two anomalous regions, $A_1$ 202 and $A_2$ 204. Anomaly $A_1$ 202 lies substantially within one plane 500 of the object 200, while anomaly $A_2$ 204 lies substantially within another plane 502 of the object 200; is the second plane 502 being located at a deeper depth with respect to the sensor plate 104. As mentioned above, the subset is an 8×8 array, such as the quadrant $Q_1$ 181, and has sensor elements 108 at locations:

$$\begin{bmatrix} (X_1, Y_1) & (X_2, Y_1) & (X_3, Y_1) & (X_4, Y_1) & \ldots & (X_8, Y_1) \\ (X_1, Y_2) & (X_2, Y_2) & (X_3, Y_2) & (X_4, Y_2) & \ldots & (X_8, Y_2) \\ (X_1, Y_3) & (X_2, Y_3) & (X_3, Y_3) & (X_4, Y_3) & \ldots & (X_8, Y_3) \\ (X_1, Y_4) & (X_2, Y_4) & (X_3, Y_4) & (X_4, Y_4) & \ldots & (X_8, Y_4) \\ \vdots & \vdots & \vdots & \vdots & \ddots & \vdots \\ (X_1, Y_8) & (X_2, Y_8) & (X_3, Y_8) & (X_4, Y_8) & \ldots & (X_8, Y_8) \end{bmatrix}$$

Figure 5B:
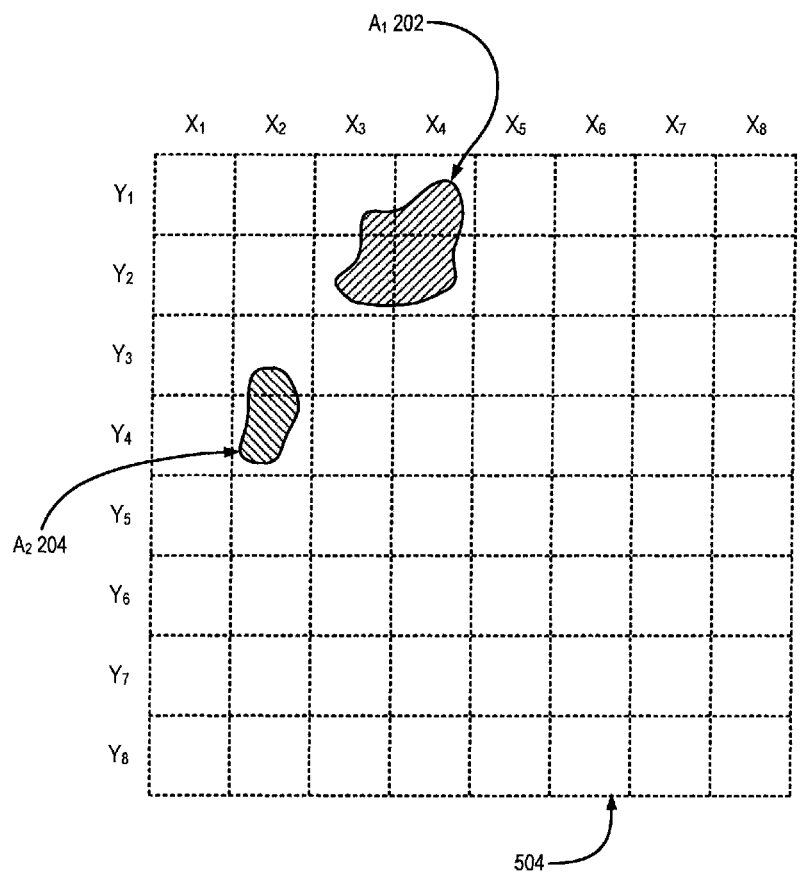
FIG. 5B is a graphic representation of the spatial location of two anomalous regions contained within the example object shown in FIG. 5A relative to a sensor element array that forms a part of the system of FIG. 1.
Figure 6A:
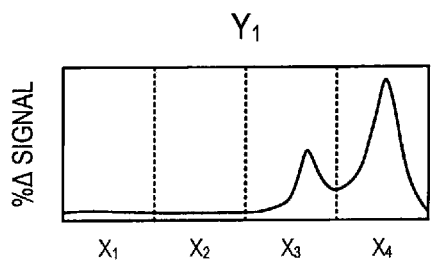
FIG. 6A is a graphic representation of difference signals corresponding to signals measured from the example object shown in FIG. 5A when practicing a method of the present invention.
Figure 6E:
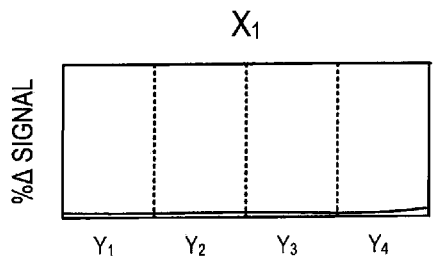
FIG. 6E is a graphic representation of difference signals corresponding to signals measured from the example object shown in FIG. 5A when practicing a method of the present invention.
Figure 6B:
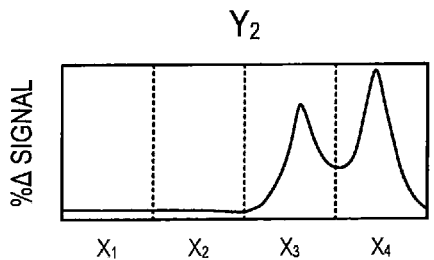
FIG. 6B is a graphic representation of difference signals corresponding to signals measured from the example object shown in FIG. 5A when practicing a method of the present invention.
Figure 6F:
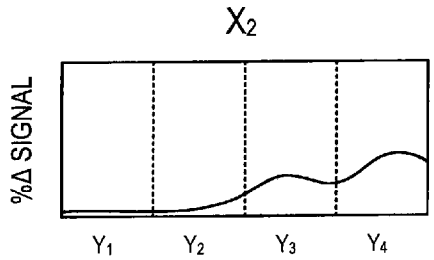
FIG. 6F is a graphic representation of difference signals corresponding to signals measured from the example object shown in FIG. 5A when practicing a method of the present invention.
Figure 6C:
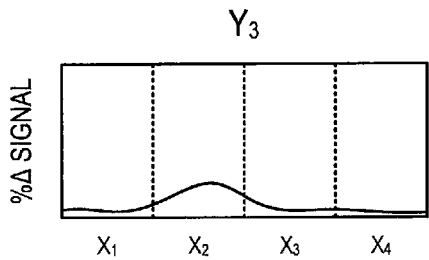
FIG. 6C is a graphic representation of difference signals corresponding to signals measured from the example object shown in FIG. 5A when practicing a method of the present invention.
Figure 6G:
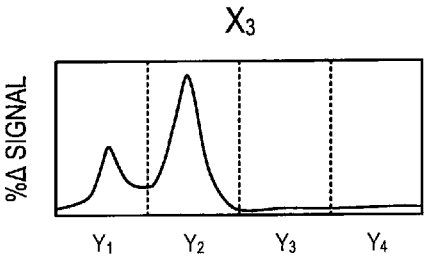
FIG. 6G is a graphic representation of difference signals corresponding to signals measured from the example object shown in FIG. 5A when practicing a method of the present invention.
Figure 6D:
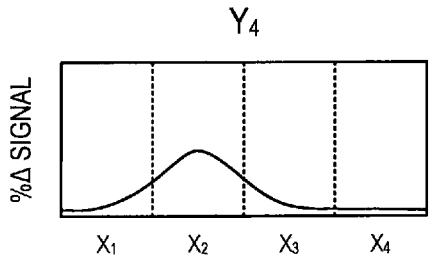
FIG. 6D is a graphic representation of difference signals corresponding to signals measured from the example object shown in FIG. 5A when practicing a method of the present invention.
Figure 6H:
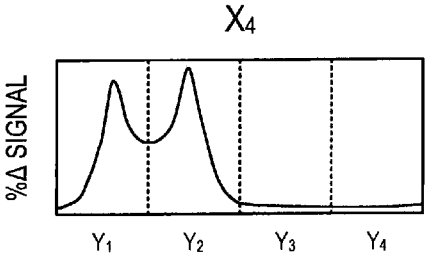
FIG. 6H is a graphic representation of difference signals corresponding to signals measured from the example object shown in FIG. 5A when practicing a method of the present invention.

Using the above labeling scheme, and referring now to FIG. 5B, when a voltage is applied to the drive plate 102 anomaly $A_1$ 202 produces signals that are detected substantially in the sensor elements 108 located at $(X_3, Y_1)$, $(X_3, Y_2)$, $(X_4, Y_1)$, and $(X_4, Y_2)$. Likewise, anomaly $A_2$ 204 produces signals that are detected substantially in sensor elements 108 located at $(X_2, Y_3)$ and $(X_2, Y_4)$. It should be noted that FIG. 5B illustrates the spatial relationship between the anomalies $A_1$ 202 and $A_2$ 204, and the sensor elements 108. As described above, in this example, the anomalies $A_1$ 202 and $A_2$ 204 are located at different depths with respect to the sensor plate 104.

Turning now to FIGS. 6A-6H, the process for determining the spatial locations of the anomalies $A_2$ 202 and $A_2$ 204 with respect to the sensor elements 108 is described. In general, the spatial position of an anomaly is determined by analyzing which sensor elements 108 produce an extrema in the measured signals. In the one configuration, a difference signal is produced by removing a baseline signal from the measured signals. The result is a signal that has local maxima for each anomaly present. For example, and making reference to the example provided in FIG. 5B, anomaly $A_1$ 202 produces a signal change in the sensor elements 108 located at $(X_3,Y_1)$, $(X_3,Y_2)$, $(X_4,Y_1)$, and $(X_4,Y_2)$. The resultant signal change is therefore detected substantially by the sensor elements 108 at these locations and the location of anomaly $A_1$ 202 is registered to the spatial locations of said sensor elements 108. More specifically, the sensor element 108 located at $(X_3,Y_1)$ is shown in the third quadrant of the plot shown in FIG. 6A, and also in the first quadrant of the plot shown in FIG. 6G. The local maxima detected by the sensor element 108 at this location therefore indicates that the anomaly $A_1$ 202 exists at least at the spatial location of the sensor element 108. In this way, a location is determined for each local maxima in the measured signal change relative to the baseline, and in one configuration is automatically registered to the corresponding spatial location in a mammographic image produced by a mammography imaging system. This x-y coordinate indicates where the anomaly is located in the parallel to the sensor plate 104, but not the depth within the object.

Figure 7A:
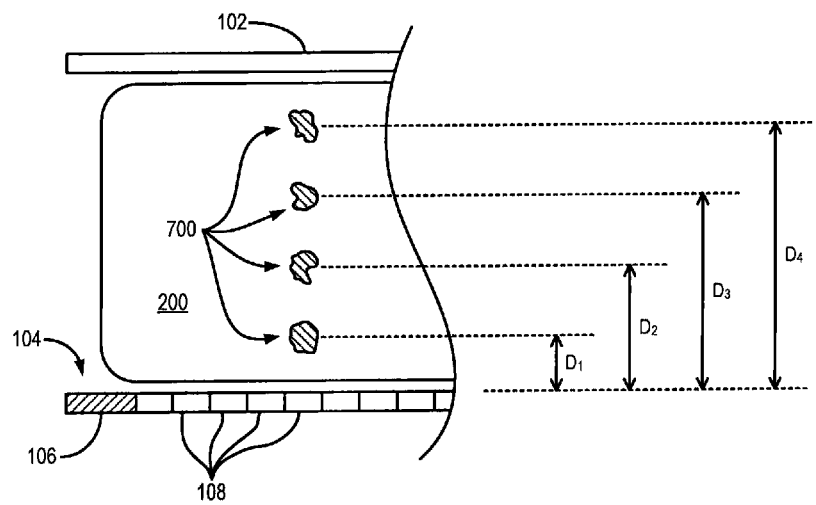
FIG. 7A is a graphic representation of a cross-section of the system of FIG. 1 and an example object under examination that contains four anomalous regions at four respective different depths within the object.
Figure 7B:
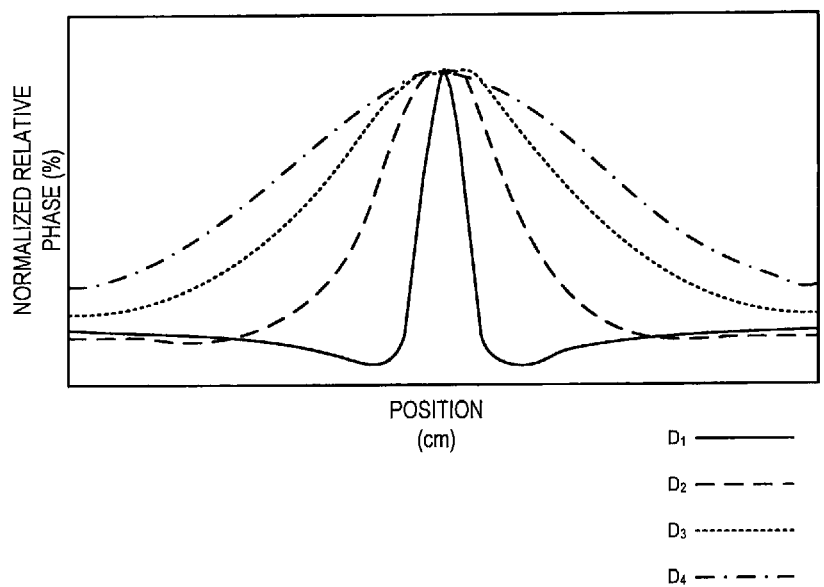
FIG. 7B is a graphic representation of a plurality of normalized difference signals indicative of the depths of the anomalous regions in the object shown in FIG. 7A.

The depth of the anomaly is determined by analyzing the peak width of each local maxima in the difference signal. Accordingly, a wider peak width indicates a deeper location with respect to the sensor element 108 in which the signal is measured. For example, and referring still to FIGS. 5B and 6A-6H, the anomaly $A_2$ 204 is at a deeper location than anomaly $A_1$ 202, resulting in measured signal changes having a wider peak. In the example provided in FIG. 5B, anomaly $A_2$ 204 produces a signal change in the sensor elements 108 located at $(X_2,Y_3)$ and $(X_2,Y_4)$. These signal changes can be seen, respectively, in the third and fourth quadrants of the plot shown in FIG. 6F, and also in the second quadrants shown in the plots in FIGS. 6C and 6D, respectively. In general, the depth of an anomaly is determined by normalizing each local maxima in the difference signal and then calculating the full-width at half-maximum of the resultant normalized signal. An example scenario is presented in FIG. 7A, where an object 200 contains four anomalous regions 700, each region at a different depth $(D_1,D_2,D_3,D_4)$ with respect to the sensor plate 104, such that $D_1<D_2<D_3<D_4$. As the anomalies get deeper within an object with respect to a sensor element 108, the corresponding local maxima in the normalized difference signals have a wider peak, and thus a greater full-width at half-maximum value. This is illustrated in FIG. 7B for the example scenario provided in FIG. 7A. The depth of an anomaly in an object can therefore be determined in the above manner by first calculating the full-width at half-maximum values for each local maxima in the difference signals. The calculated full-width at half-maximum values are then correlated to predetermined depths, thus providing information indicative of the depth of each anomaly.

Figure 8:
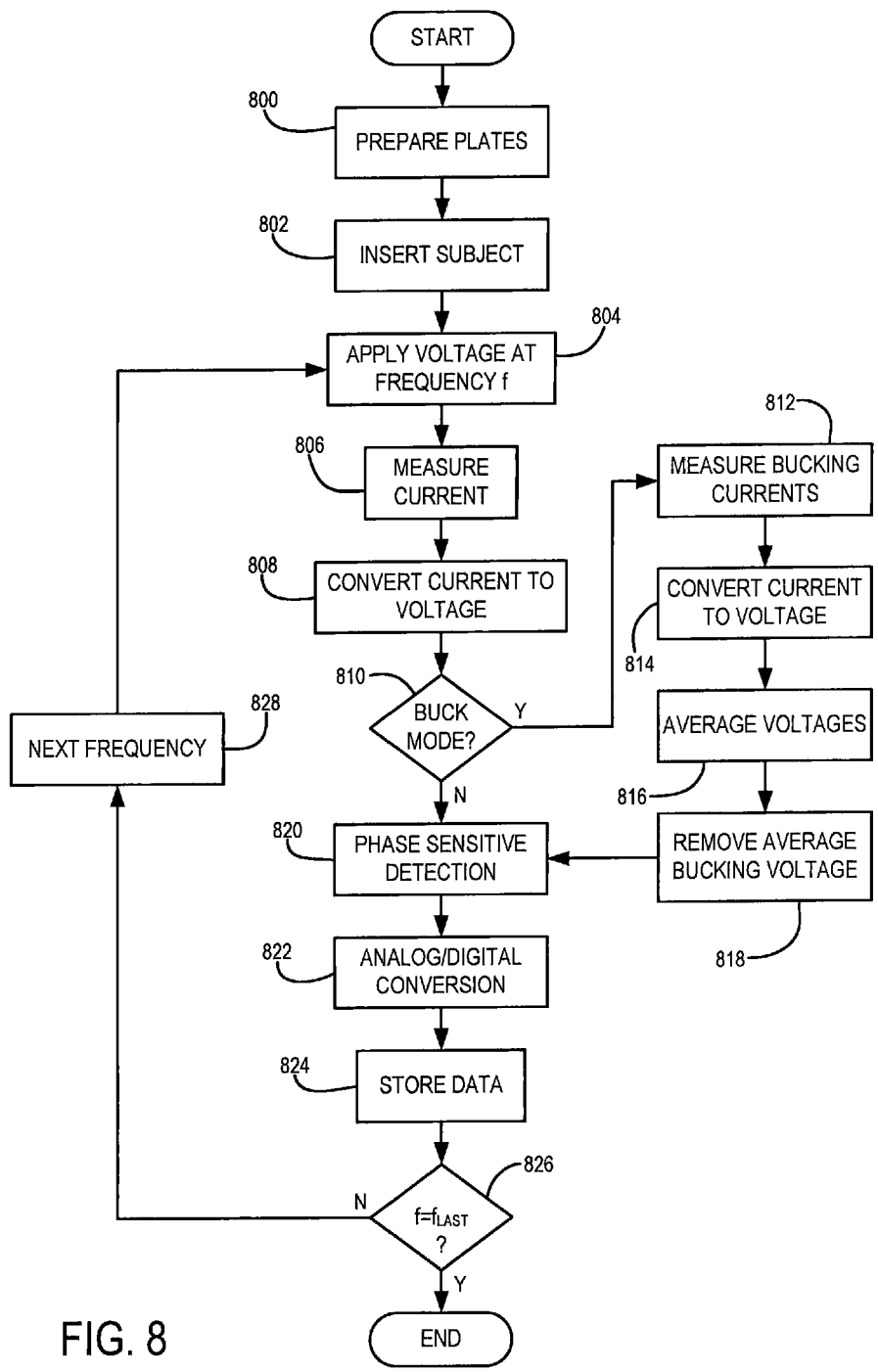
FIG. 8 is a flowchart setting forth the steps of a data acquisition process employed by the system of the present invention.

A general method for acquiring data with the system of the present invention is presented in FIG. 8 with reference to the structural components of the systems illustrated in FIGS. 1-5A. First, the sensor plate 104 and drive plate 102 are prepared for the study, as indicated at step 800. This step includes applying an electrically conductive jelly to the surface of both plates in order to facilitate the flow of electricity through the object 200 of the examination. The drive plate 102 and sensor system 100 can alternatively be translated and rotated in space to obtain a more preferable orientation with respect to the object 200. In one embodiment, this is achieved by the means for rotation and translation provided by the mammography system 400 with which the sensor system 100 and drive system 102 are integrated. After the plates have been prepared, the object is placed into position between the two plates, as shown in step 802, and the examination begins. The plates are brought into electrical contact with the object; however, in one configuration, the compression paddle 402 to which the drive plate 102 is integrated acts to compress the subject's breast as is common practice during a mammographic study. In the alternative, conventional mammographic images can be acquired at this time.

The examination then progresses by applying a time-varying sinusoidal voltage with a selected frequency, f, to the drive plate 102, as indicated at step 804. This voltage produces an electric field that extends through the object 200. The result of this applied voltage and generated electric field is to induce charge accumulations at the boundaries between regions within the object 200 that have different electrical properties. These charges are then measured as currents in the array of sensor elements 108, as indicated at step 806. The measured currents are converted to voltage signals in step 808 by employing current-to-voltage converters 142. The system of the present invention has the option to operate in a current bucking mode. If the operator selects the current bucking mode, then this mode is entered into at decision block 810. The first step in the current bucking mode is to measure a plurality of bucking currents, as indicated in step 812. The bucking currents are measured in the four sensor elements 108 having the locations:

$[(X_7,Y_2)(X_8,Y_2)(X_9,Y_2)(X_{10},Y_2)]$,

That is, the four sensor elements 108 corresponding to the horizontal center of the array that are one row in from the object 200 under examination. These measured currents are converted to voltage signals in step 814, again employing the current-to-voltage converters 142. An average bucking voltage is then determined by averaging the determined voltage signals, as indicated at step 816. Both the in-phase and quadrature components of the average bucking voltage are then subtracted from each voltage signal determined in step 808. The bucking voltage value is stored and saved for use during data processing.

As shown in step 820, the general data acquisition method proceeds by employing phase sensitive detection of the voltage signals, which acts to average out DC offset and phase errors in the measured signals. This step employs the use of a phase sensitive detector. The resultant signals are then converted from analog to digital by an A/D converter 146, as indicated in step 822. The digital signals are then stored in the memory buffer 130. Additional measurements are made with applied voltages having different frequencies until all of the desired selected frequencies have been utilized, as decided at decision block 826. If all of the desired frequencies have not been employed, a new frequency is selected at step 828 and the data acquisition process proceeds in the above manner. In the preferred embodiment, a range of applied voltage frequencies, which includes 10 KHz to 2 MHz, is employed. After all of the desired data has been acquired and stored, it is sent to the computer controller system storage 154 for further processing. Likewise, if the bucking mode was employed at step 810, then the average bucking voltage determined at step 816 for the selected frequency, f, is also converted to a digital signal and stored to memory buffer 130 before being transferred to the computer controller system storage 154.

Figure 9:
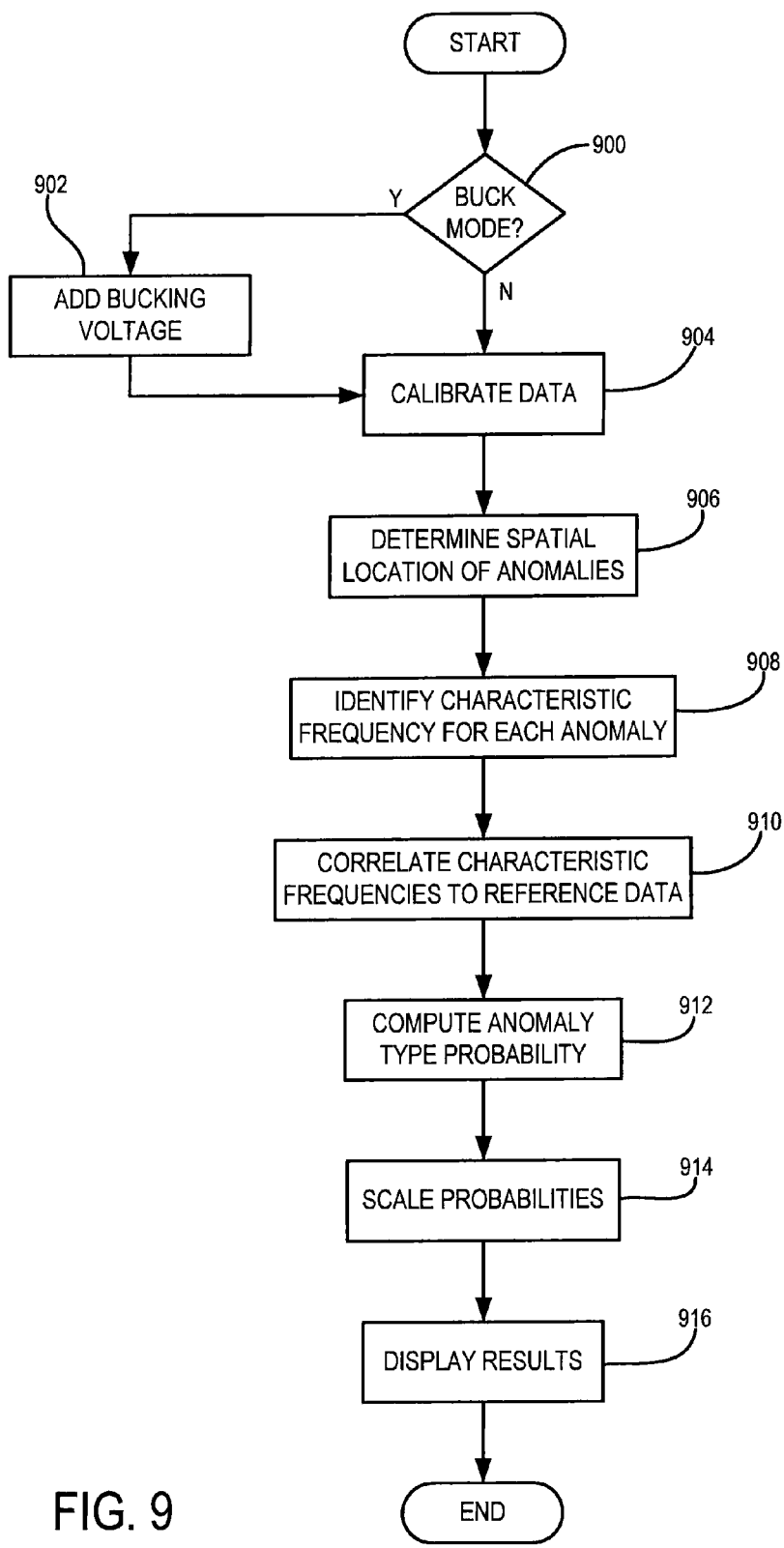
FIG. 9 is a flowchart setting forth the steps of an analysis method of the present invention.

Referring particularly to FIG. 9 and with reference to the structural components of the systems illustrated in FIGS. 1-5A, the data processing method begins at step 900 by determining whether the bucking mode was selected by the operator in step 810 of the data acquisition process. If the bucking mode was utilized during data acquisition, the stored average bucking voltage determined in step 816 is added back to the voltage signals in step 902. The data processing then proceeds at step 904 where the signal data is calibrated by employing previously generated calibration data. The calibration data is produced by operating the system of the present invention without the object 200 present. A known current is applied to each of the sensor elements 108 with a standard electrical probe connected through a resistor having a known value. The measured reference currents at each sensor element 108 are then converted into a reference voltage signal through the process described above in reference to FIG. 8, and stored in a calibration file. A set of calibration data is acquired in this way for each of the desired voltage frequencies. The acquired calibration data is subsequently normalized, then used to correct both the magnitude and phase of the current data. Magnitude correction includes producing a correction term that includes an array of scaling factors. That is, one scaling factor is produced for each sensor element 108. These magnitude correction factors are multiplied to the magnitude of the measured current signal in each sensor element 108. Likewise, a phase correction term is produced that includes an array of scaling factors as well. The phase correction factors are subsequently subtracted from the measured current signal acquired from the corresponding sensor elements 108.

Analysis of the measured signals now proceeds by first determining the spatial locations of anomalies within the measured signal data, as indicated in step 906. This process is performed as described above in reference to FIGS. 5B and 6A-6H. The sensor element 108 in which a peak signal change is detected describes the spatial location of the anomaly in the transverse, or x-y, plane. Next, the spatial location of the anomaly along the z-axis (that is, the depth) is determined as described above in reference to FIGS. 7A and 7B. By correlating the width of each peak signal change with predetermined values, the spatial location of the anomaly is determined in the z-direction. The complete spatial location of each detected anomaly is determined in this manner. In one configuration, the spatial locations of the anomalies are automatically co-registered to a mammographic image. In this way, a more accurate clinical diagnosis can be achieved. In fact, the anomalies detected with the system of the present invention are not necessarily visually detectable or discernable in a conventional mammographic image, thus providing an improvement over conventional breast cancer screening examinations.

Figure 10:
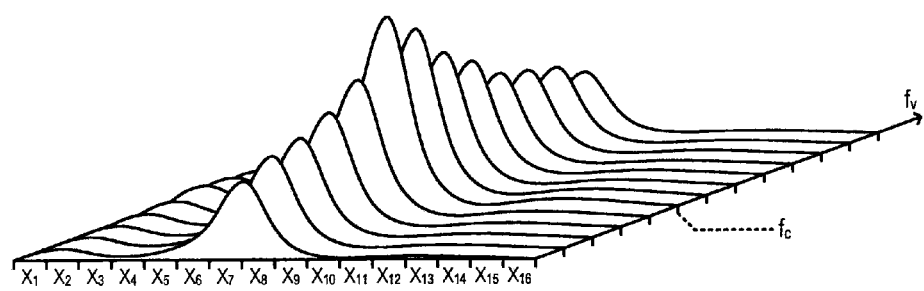
FIG. 10 is a graphic representation of a plot of difference signals measured by a row of sensor elements versus frequencies of a time-varying voltage applied to a subject in order to generate measured signals.

After the spatial locations of the anomalies have been determined, the characterization of each anomaly as one of a particular disease state begins. First, as shown in step 908, a "characteristic frequency" for each anomaly is identified in the difference signals. In this process, the local maxima in the difference signals for data corresponding to a first applied voltage frequency are compared to subsequent difference signals corresponding to measurements made after the application of the time-varying voltage to the drive plate 102 at different applied voltage frequencies. For a given spatial location, and therefore a given anomaly, the applied voltage frequency at which the greatest local maxima occurs is recorded. This process can be performed on either or both of the in-phase or quadrature component of the difference signals, but is preferably performed on the quadrature component. An example of a series of difference signals is shown in FIG. 10 where the difference signals corresponding to a row of sensor elements 108 having spatial locations ($X_1, \ldots, X_{16}$) are shown for a plurality of applied time-varying voltage frequencies, $f_v$. The anomaly indicated in the sensor elements 108 $X_7, X_8$, produces a peak difference signal when measured with the applied time-varying voltage frequency, $f_c$. Thus, for this example data, the frequency $f_c$ is recorded as the characteristic frequency for the anomaly indicated in the difference signals.

Once the characteristic frequency of each anomaly has been determined in this way, the characterization process proceeds by correlating each characteristic frequency with reference data, as indicated at step 910. The reference data includes stored frequency data for a plurality of different known disease states. A correlation coefficient is calculated between each characteristic frequency and the reference data. The correlation coefficients have values from 0 to 1, and indicate the degree of correlation between an anomaly having a given characteristic frequency and a particular disease state indicated in the reference data. For example, if an identified characteristic frequency, $f_c$, produces a correlation coefficient of 0.95 with respect to reference data corresponding to ductal carcinoma in situ (DCIS), then there is a high probability that the anomaly associated with that characteristic frequency is also DCIS. The actual probability that the anomaly is of a particular disease state is calculated in step 912. Here, the following probability is computed:

$$P_X(c_i) = e^{-0.5\left(\frac{c_i - \bar{c}}{\sigma(c)}\right)^2},$$

Where X is the anomaly type, $c_i$ is the correlation coefficient for the $i^{th}$ characteristic frequency, $\bar{c}$ is the average of all the correlation coefficients, and $\sigma(c)$ is the standard deviation of all the correlation coefficients. The determined probabilities are then scaled by a decision constant, $K_T$, in step 914. The decision constant, $K_T$, is chosen to substantially minimize either false positives or false negatives for a given tissue type, T. The results of the characterization process are then displayed on display 170, as indicated at step 916.

These results can either be displayed as a text-based list describing the presence of cancerous regions, or more beneficially, as an image indicative of the identified disease state. For example, an image can be produced with each pixel in the image corresponding to a sensor element 108. The values of the pixels in the image are then set corresponding to the disease state of the portion of the subject under examination. For example, those regions identified as cancerous could be given a red pixel value, those regions identified as precancerous could be given an orange pixel value, and those regions identified as healthy could be given a green pixel value. Additionally, a color scale that varies from, say, yellow to red can be applied based on the probability calculated in step 914.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for identifying an anomalous region in a portion of a subject and determining a disease state thereof, the steps comprising:
   a) applying an electrical power to the subject;
   b) varying the magnitude of an electrical characteristic of the electrical power at a selected frequency;

c) acquiring, with a plurality of sensor elements, signals indicative of a second electrical characteristic resulting from the electrical power that is applied to the subject;

d) determining an in-plane spatial location of at least one anomalous region within the subject by calculating a local extremum of the signals acquired in step c) and determining which one of the plurality of sensor elements acquired a portion of the signals acquired in step c) that contains the calculated local extremum;

e) characterizing the at least one anomalous region as one of a particular disease state by comparing the signals acquired in step c) to reference signal information;

f) generating a report indicating the in-plane spatial location and the disease state of the anomalous regions within the portion of the subject; and wherein step d) includes determining a depth of the at least one anomalous region by calculating a width of the local extremum.

2. The method as recited in claim 1 in which step e) includes:

e)i) determining, from the signals acquired in step c), a characteristic frequency of a selected anomalous region.

3. The method as recited in claim 2 in which step e) further includes:

e)ii) calculating, from the characteristic frequency determined in step e)i) and the reference signal information, a probability that the selected anomalous region is a particular disease state.

4. The method as recited in claim 3 in which the calculated probability is scaled by a decision constant that substantially suppresses at least one of false positives and false negatives.

5. The method as recited in claim 1 in which the electrical characteristic of the electrical power is a voltage and in which the second electrical characteristic is a current.

6. The method as recited in claim 1 in which the electrical characteristic of the electrical power is a current and in which the second electrical characteristic is a voltage.

* * * * *